United States Patent
Drake et al.

(10) Patent No.: US 12,178,470 B2
(45) Date of Patent: Dec. 31, 2024

(54) EXTRAVASCULAR IMPLANT TOOLS UTILIZING A BORE-IN MECHANISM AND IMPLANT TECHNIQUES USING SUCH TOOLS

(71) Applicant: Medtronic, Inc., Minneapolis, MN (US)

(72) Inventors: Ronald A. Drake, St. Louis Park, MN (US); Kevin R. Seifert, Forest Lake, MN (US); Lester O. Stener, Hudson, WI (US); Amy E. Thompson-Nauman, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 134 days.

(21) Appl. No.: 17/397,276

(22) Filed: Aug. 9, 2021

(65) Prior Publication Data

US 2022/0061886 A1    Mar. 3, 2022

Related U.S. Application Data

(63) Continuation of application No. 14/962,485, filed on Dec. 8, 2015, now Pat. No. 11,083,491.
(Continued)

(51) Int. Cl.
*A61B 17/34* (2006.01)
*A61M 25/01* (2006.01)
(Continued)

(52) U.S. Cl.
CPC ..... *A61B 17/3468* (2013.01); *A61M 25/0194* (2013.01); *A61N 1/0573* (2013.01);
(Continued)

(58) Field of Classification Search
CPC .... A61B 17/3468; A61B 2017/320056; A61N 1/0573; A61N 1/0592; A61N 1/05; A61M 25/0194
See application file for complete search history.

(56) References Cited

U.S. PATENT DOCUMENTS

| | | | |
|---|---|---|---|
| 4,030,509 A | 6/1977 | Heilman et al. | |
| 4,146,037 A | 3/1979 | Flynn et al. | |

(Continued)

FOREIGN PATENT DOCUMENTS

| | | | |
|---|---|---|---|
| CN | 2364868 Y | 2/2000 | |
| CN | 101072601 A | 11/2007 | |

(Continued)

OTHER PUBLICATIONS

Avogadros Lab Supply Inc., Catalog; Scoopula with Beech Wood Handle, can be found on-line at http://www.avogadro-lab-supply.com/search.php, accessed Oct. 6, 2013, 1 page.
(Continued)

*Primary Examiner* — Katherine M Rodjom
(74) *Attorney, Agent, or Firm* — Shumaker & Sieffert, P.A.

(57) ABSTRACT

Extravascular implant tools that utilize a bore-in mechanism to safely access extravascular locations and implant techniques utilizing these tools are described. The bore-in mechanism may include a handle and a helix extending from the handle. The bore-in mechanism is used, for example, in conjunction with a tunneling tool to traverse the diaphragmatic attachments to access a substernal location. The tunneling tool may be an open channel tunneling tool or a conventional tunneling tool (e.g., metal rod).

19 Claims, 10 Drawing Sheets

Related U.S. Application Data

(60) Provisional application No. 62/089,489, filed on Dec. 9, 2014.

(51) Int. Cl.
*A61N 1/05* (2006.01)
*A61B 17/32* (2006.01)

(52) U.S. Cl.
CPC ................................ *A61N 1/0592* (2013.01); *A61B 2017/320056* (2013.01); *A61N 1/0504* (2013.01); *A61N 1/0563* (2013.01)

(56) References Cited

U.S. PATENT DOCUMENTS

| | | | |
|---|---|---|---|
| 4,207,903 A | 6/1980 | O'neill | |
| 4,270,549 A | 6/1981 | Heilman | |
| 4,280,510 A | 7/1981 | O'Neill | |
| 4,291,707 A | 9/1981 | Heilman et al. | |
| 4,424,818 A | 1/1984 | Doring et al. | |
| 4,437,475 A | 3/1984 | White | |
| 4,512,351 A | 4/1985 | Pohndorf | |
| 4,538,624 A | 9/1985 | Tarjan | |
| 4,644,957 A | 2/1987 | Ricciardelli et al. | |
| 4,765,341 A | 8/1988 | Mower et al. | |
| 4,832,687 A | 5/1989 | Smith, III | |
| 4,874,374 A | 10/1989 | Kousai et al. | |
| 4,921,479 A | 5/1990 | Grayzel | |
| 5,009,643 A | 4/1991 | Reich et al. | |
| 5,036,854 A | 8/1991 | Schollmeyer et al. | |
| 5,125,904 A | 6/1992 | Lee | |
| 5,147,376 A | 9/1992 | Pianetti | |
| 5,176,135 A | 1/1993 | Fain et al. | |
| 5,255,691 A | 10/1993 | Otten | |
| 5,257,973 A | 11/1993 | Villasuso | |
| 5,258,003 A | 11/1993 | Ciaglia et al. | |
| 5,300,106 A | 4/1994 | Dahl et al. | |
| 5,312,355 A | 5/1994 | Lee | |
| 5,346,502 A | 9/1994 | Estabrook et al. | |
| 5,364,372 A | 11/1994 | Danks et al. | |
| 5,441,504 A | 8/1995 | Pohndorf et al. | |
| 5,456,699 A | 10/1995 | Armstrong | |
| 5,478,329 A | 12/1995 | Ternamian | |
| 5,509,924 A | 4/1996 | Paspa et al. | |
| 5,613,953 A | 3/1997 | Pohndorf | |
| 5,667,514 A | 9/1997 | Heller | |
| 5,671,736 A | 9/1997 | Pettit et al. | |
| 5,690,648 A | 11/1997 | Fogarty et al. | |
| 5,752,937 A | 5/1998 | Otten et al. | |
| 5,755,697 A | 5/1998 | Jones et al. | |
| 5,779,715 A | 7/1998 | Tu | |
| 5,782,841 A | 7/1998 | Ritz et al. | |
| 5,800,398 A | 9/1998 | Hahnle et al. | |
| 5,853,391 A | 12/1998 | Bell | |
| 5,871,528 A | 2/1999 | Camps et al. | |
| 5,871,532 A | 2/1999 | Schroeppel | |
| 5,944,732 A | 8/1999 | Raulerson et al. | |
| 5,951,518 A | 9/1999 | Licata et al. | |
| 6,032,079 A | 2/2000 | KenKnight et al. | |
| 6,104,957 A | 8/2000 | Alo et al. | |
| 6,122,552 A | 9/2000 | Tockman et al. | |
| 6,159,198 A | 12/2000 | Gardeski et al. | |
| 6,228,052 B1 | 5/2001 | Pohndorf | |
| 6,278,897 B1 | 8/2001 | Rutten et al. | |
| 6,283,948 B1 | 9/2001 | McKernan et al. | |
| 6,324,414 B1 | 11/2001 | Gibbons et al. | |
| 6,415,187 B1 | 7/2002 | Kuzma et al. | |
| 6,436,068 B1 | 8/2002 | Bardy | |
| 6,445,954 B1 | 9/2002 | Olive et al. | |
| 6,544,247 B1 | 4/2003 | Gardeski et al. | |
| 6,605,094 B1 | 8/2003 | Mann | |
| 6,726,617 B1 | 4/2004 | Schmidt | |
| 6,730,083 B2 | 5/2004 | Freigang et al. | |
| 6,733,500 B2 | 5/2004 | Kelley et al. | |
| 6,749,574 B2 | 6/2004 | O'Keefe | |
| 6,770,070 B1 | 8/2004 | Balbierz | |
| 6,772,014 B2 | 8/2004 | Coe et al. | |
| 6,836,687 B2 | 12/2004 | Kelley et al. | |
| 6,866,044 B2 | 3/2005 | Bardy et al. | |
| 6,868,291 B1 | 3/2005 | Booner et al. | |
| 6,887,229 B1 | 5/2005 | Kurth | |
| 7,001,396 B2 | 2/2006 | Glazier et al. | |
| 7,018,384 B2 | 3/2006 | Skakoon | |
| 7,033,326 B1 | 4/2006 | Pianca et al. | |
| 7,069,083 B2 | 6/2006 | Finch et al. | |
| 7,076,296 B2 | 7/2006 | Rissmann et al. | |
| 7,117,039 B2 | 10/2006 | Manning et al. | |
| 7,151,965 B2 | 12/2006 | Osypka | |
| 7,194,309 B2 | 3/2007 | Ostroff et al. | |
| 7,195,637 B2 | 3/2007 | Mika | |
| 7,218,970 B2 | 5/2007 | Ley et al. | |
| 7,229,450 B1 | 6/2007 | Chitre et al. | |
| 7,288,096 B2 | 10/2007 | Chin | |
| 7,316,667 B2 | 1/2008 | Linstrom et al. | |
| 7,322,960 B2 | 1/2008 | Yamamoto et al. | |
| 7,361,169 B2 | 4/2008 | Reilly | |
| 7,369,899 B2 | 5/2008 | Malinowski et al. | |
| 7,389,134 B1 | 6/2008 | Karicherla et al. | |
| 7,450,997 B1 | 11/2008 | Pianca et al. | |
| 7,499,758 B2 | 3/2009 | Cates et al. | |
| 7,499,759 B2 | 3/2009 | Cates et al. | |
| 7,539,542 B1 | 5/2009 | Malinowski | |
| 7,627,375 B2 | 12/2009 | Bardy et al. | |
| 7,655,014 B2 | 2/2010 | Ko et al. | |
| 7,736,309 B2 | 6/2010 | Miller et al. | |
| 7,736,330 B2 | 6/2010 | Bardy | |
| 7,758,590 B2 | 7/2010 | Daniele et al. | |
| 7,765,014 B2 | 7/2010 | Eversull et al. | |
| 7,837,671 B2 | 11/2010 | Eversull et al. | |
| 7,846,088 B2 | 12/2010 | Ness | |
| 7,890,191 B2 | 2/2011 | Rutten et al. | |
| 7,930,040 B1 | 4/2011 | Kelsch et al. | |
| 7,983,765 B1 | 7/2011 | Doan et al. | |
| 8,012,127 B2 | 9/2011 | Lieberman et al. | |
| 8,057,486 B2 | 11/2011 | Hansen | |
| 8,060,207 B2 | 11/2011 | Wallace et al. | |
| 8,065,020 B2 | 11/2011 | Ley et al. | |
| 8,066,702 B2 | 11/2011 | Rittman, III et al. | |
| 8,090,451 B2 | 1/2012 | Tyson, Jr. | |
| 8,155,755 B2 | 4/2012 | Flynn et al. | |
| 8,157,813 B2 | 4/2012 | Ko et al. | |
| 8,260,436 B2 | 9/2012 | Gerber et al. | |
| 8,271,094 B1 | 9/2012 | Moffitt | |
| 8,280,527 B2 | 10/2012 | Eckerdal et al. | |
| 8,340,779 B2 | 12/2012 | Harris et al. | |
| 8,340,781 B2 | 12/2012 | Konishi | |
| 8,355,786 B2 | 1/2013 | Malinowski | |
| 8,364,277 B2 | 1/2013 | Glukhovsky | |
| 8,386,052 B2 | 2/2013 | Harris et al. | |
| 8,409,233 B1 | 4/2013 | Chinn et al. | |
| 8,435,208 B2 | 5/2013 | Bardy | |
| 8,442,620 B2 | 5/2013 | Silipo et al. | |
| 8,447,396 B2 | 5/2013 | Palti et al. | |
| 8,447,398 B2 | 5/2013 | Bardy et al. | |
| 8,452,421 B2 | 5/2013 | Thenuwara et al. | |
| 8,454,552 B2 | 6/2013 | Bardy | |
| 8,478,424 B2 | 7/2013 | Tronnes | |
| 8,478,426 B2 | 7/2013 | Barker | |
| 8,942,820 B2 | 1/2015 | Doerr et al. | |
| 8,986,278 B2 | 3/2015 | Fung et al. | |
| 9,227,053 B2 | 1/2016 | Bonde et al. | |
| 9,610,436 B2 | 4/2017 | Seifert et al. | |
| 10,118,027 B2 | 11/2018 | Seifert et al. | |
| 10,349,978 B2 | 7/2019 | Seifert et al. | |
| 10,531,893 B2 | 1/2020 | Seifert et al. | |
| 10,792,490 B2 | 10/2020 | Seifert et al. | |
| 11,083,491 B2 | 8/2021 | Drake et al. | |
| 2002/0068912 A1 | 6/2002 | Merdan | |
| 2002/0072712 A1 | 6/2002 | Nool et al. | |
| 2002/0120277 A1 | 8/2002 | Hauschild | |
| 2002/0120294 A1 | 8/2002 | Kroll | |
| 2002/0143251 A1 | 10/2002 | Richardson | |
| 2002/0147484 A1 | 10/2002 | Dahl et al. | |
| 2003/0114908 A1 | 6/2003 | Flach | |

(56) References Cited

U.S. PATENT DOCUMENTS

| | | |
|---|---|---|
| 2003/0233115 A1 | 12/2003 | Eversull et al. |
| 2004/0054388 A1* | 3/2004 | Osypka .................. A61N 1/056 607/116 |
| 2004/0059348 A1 | 3/2004 | Geske et al. |
| 2004/0064147 A1 | 4/2004 | Struble |
| 2004/0087970 A1 | 5/2004 | Chu et al. |
| 2004/0102829 A1 | 5/2004 | Bonner et al. |
| 2004/0124389 A1 | 7/2004 | Phillips |
| 2004/0147940 A1 | 7/2004 | Crawford |
| 2004/0176781 A1 | 9/2004 | Lindstrom |
| 2004/0210293 A1 | 10/2004 | Bardy et al. |
| 2004/0236396 A1 | 11/2004 | Coe et al. |
| 2005/0049663 A1 | 3/2005 | Harris et al. |
| 2005/0119680 A1 | 6/2005 | Dykes |
| 2005/0131505 A1 | 6/2005 | Yokoyama |
| 2005/0288758 A1 | 12/2005 | Jones et al. |
| 2006/0041295 A1 | 2/2006 | Okypka |
| 2006/0116746 A1 | 6/2006 | Chin |
| 2006/0122676 A1 | 6/2006 | Ko et al. |
| 2006/0155250 A1 | 7/2006 | Endo et al. |
| 2006/0253181 A1* | 11/2006 | Schulman ............ A61N 1/0551 607/116 |
| 2006/0265047 A1 | 11/2006 | Dorn |
| 2007/0066977 A1 | 3/2007 | Assell et al. |
| 2007/0083217 A1 | 4/2007 | Eversull et al. |
| 2007/0100409 A1 | 5/2007 | Worley et al. |
| 2007/0173900 A1 | 7/2007 | Siegel |
| 2007/0203553 A1 | 8/2007 | Smits |
| 2007/0208402 A1 | 9/2007 | Helland et al. |
| 2007/0239241 A1 | 10/2007 | Tyson |
| 2007/0249992 A1 | 10/2007 | Bardy |
| 2008/0046056 A1 | 2/2008 | O'Connor |
| 2008/0097424 A1 | 4/2008 | Wizeman et al. |
| 2008/0103572 A1* | 5/2008 | Gerber ................. A61N 1/0534 607/116 |
| 2008/0132933 A1 | 6/2008 | Gerber |
| 2008/0132970 A1 | 6/2008 | Barolat |
| 2008/0167650 A1 | 7/2008 | Joshi et al. |
| 2008/0208133 A1 | 8/2008 | Lieberman et al. |
| 2008/0234717 A1 | 9/2008 | Bruszewski |
| 2008/0243219 A1 | 10/2008 | Malinowski et al. |
| 2008/0269716 A1 | 10/2008 | Bonde et al. |
| 2008/0269763 A1 | 10/2008 | Bonde et al. |
| 2009/0018603 A1 | 1/2009 | Mitelberg et al. |
| 2009/0043373 A1 | 2/2009 | Arnault De |
| 2009/0069750 A1 | 3/2009 | Schraga |
| 2009/0076521 A1 | 3/2009 | Hansen |
| 2009/0157091 A1 | 6/2009 | Buysman |
| 2009/0222021 A1 | 9/2009 | Chang |
| 2009/0259283 A1 | 10/2009 | Brandt et al. |
| 2009/0264780 A1 | 10/2009 | Schilling |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0056858 A1 | 3/2010 | Mokelke et al. |
| 2010/0094252 A1 | 4/2010 | Wengreen et al. |
| 2010/0113963 A1 | 5/2010 | Smits et al. |
| 2010/0125194 A1 | 5/2010 | Bonner et al. |
| 2010/0137879 A1 | 6/2010 | Ko et al. |
| 2010/0152747 A1 | 6/2010 | Padiy et al. |
| 2010/0198149 A1* | 8/2010 | Fox .................... A61B 17/3478 604/99.01 |
| 2010/0198229 A1 | 8/2010 | Olomutzki et al. |
| 2010/0217298 A1 | 8/2010 | Bardy |
| 2010/0217301 A1 | 8/2010 | Bardy |
| 2010/0249696 A1 | 9/2010 | Bardy |
| 2010/0268024 A1 | 10/2010 | Brannon |
| 2010/0305428 A1 | 12/2010 | Bonner et al. |
| 2010/0318098 A1 | 12/2010 | Lund et al. |
| 2011/0009877 A1 | 1/2011 | Thenuwara et al. |
| 2011/0009933 A1 | 1/2011 | Barker |
| 2011/0022057 A1 | 1/2011 | Eigler et al. |
| 2011/0190786 A1 | 8/2011 | Gerber et al. |
| 2011/0224680 A1 | 9/2011 | Barker |
| 2011/0224681 A1 | 9/2011 | McDonald |
| 2011/0257660 A1 | 10/2011 | Jones et al. |
| 2012/0016377 A1 | 1/2012 | Geroy |
| 2012/0029335 A1 | 2/2012 | Sudam et al. |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0191106 A1 | 7/2012 | Ko et al. |
| 2012/0209283 A1 | 8/2012 | Zhu |
| 2012/0209285 A1 | 8/2012 | Barker et al. |
| 2012/0277761 A1 | 11/2012 | Boling et al. |
| 2012/0290057 A1 | 11/2012 | Boling et al. |
| 2012/0302915 A1* | 11/2012 | Lee .................... A61B 10/0266 600/567 |
| 2013/0079693 A1 | 3/2013 | Ranky et al. |
| 2013/0103049 A1 | 4/2013 | Bonde |
| 2013/0110159 A1 | 5/2013 | Litvack et al. |
| 2013/0158564 A1 | 6/2013 | Harris et al. |
| 2013/0238067 A1 | 9/2013 | Baudino |
| 2013/0253260 A1 | 9/2013 | Lund et al. |
| 2013/0281772 A1 | 10/2013 | Fridez et al. |
| 2013/0296879 A1 | 11/2013 | Lazeroms et al. |
| 2013/0317583 A1 | 11/2013 | Pianca |
| 2014/0012292 A1 | 1/2014 | Stewart |
| 2014/0039264 A1 | 2/2014 | Heiman |
| 2014/0073926 A1 | 3/2014 | Rajendran et al. |
| 2014/0148786 A1 | 5/2014 | Milo |
| 2014/0163655 A1 | 6/2014 | Chitre |
| 2014/0194924 A1 | 7/2014 | Tegels |
| 2014/0276927 A1 | 9/2014 | Barker |
| 2014/0330208 A1 | 11/2014 | Christie et al. |
| 2014/0336581 A1 | 11/2014 | Collin |
| 2015/0032142 A1 | 1/2015 | Silvestro |
| 2015/0105793 A1 | 4/2015 | Cole |
| 2015/0133951 A1 | 5/2015 | Siefert et al. |
| 2015/0133952 A1 | 5/2015 | Seifert et al. |
| 2015/0133953 A1 | 5/2015 | Siefert et al. |
| 2015/0133954 A1 | 5/2015 | Siefert et al. |
| 2015/0216519 A1 | 8/2015 | Tang et al. |
| 2015/0313633 A1 | 11/2015 | Gross et al. |
| 2016/0157890 A1 | 6/2016 | Drake et al. |
| 2016/0158530 A1 | 6/2016 | Drake et al. |
| 2016/0175008 A1 | 6/2016 | Seifert et al. |

FOREIGN PATENT DOCUMENTS

| | | |
|---|---|---|
| CN | 101502699 A | 8/2009 |
| CN | 101742975 A | 6/2010 |
| CN | 102202726 A | 9/2011 |
| CN | 102716543 A | 10/2012 |
| CN | 102943352 A | 2/2013 |
| CN | 103096838 A | 5/2013 |
| CN | 103096963 A | 5/2013 |
| CN | 103157181 A | 6/2013 |
| CN | 103635225 A | 3/2014 |
| EP | 0517494 A2 | 12/1992 |
| WO | 9720530 A1 | 6/1997 |
| WO | 2001023035 A1 | 4/2001 |
| WO | 2004073506 A2 | 9/2004 |
| WO | 2010045228 A2 | 4/2010 |
| WO | 2012032147 A2 | 3/2012 |
| WO | 2012106088 A2 | 8/2012 |
| WO | 2013076213 A1 | 5/2013 |

OTHER PUBLICATIONS

Bielefeld et al., "Thoracoscopic Placement of Implantable Cardioverter-Defibrillator Patch Leads in Sheep," Circulation; Nov. 1993, vol. 88, Part 2; 5 pages.

Bolling et al., "Automatic Internal Cardioverter Defibrillator: A Bridge to Heart Transplantation," Heart Lung Transplantation, Abstract Only, Jul.-Aug. 1991, 1 page.

Boston Scientific, "Emblem S-ICD Subcutaneous Electrode Insertion Tool", Model 4711 User Manual, Feb. 1, 2015, accessed from https://web.archive.org/web/20151025171513/https://www.bostonscientific.com/manuals/manuals/landing-page/US-english.html, 28 pp.

(56) References Cited

OTHER PUBLICATIONS (PCT/US2015/064599) PCT International Preliminary Report on Patentability, Mailed Jun. 13, 2017, 8 pages.
(PCT/US2015/064599) PCT Notification of Transmittal of the International Search Report and the Written Opinion of the International Searching Authority, Mailed Mar. 15, 2016, 13 pages.
Cigna et al., "A New Technique for Substernal Colon Transposition with a Brest Dissector: Report of 39 Cases," Journal of Plastic, Reconstructive and Aesthetic Surgery, Apr. 2006; 59, 4 pages.
Damiano, "Implantation of Cardioverter Defibrillators in the Post-Sternotomy Patient," The Annals of Thoracic Surger, Jun. 1, 1992; 53: pp. 978-983.
Ely et al., "Thorasoscopic Implantation of the Implantable Cardioverter Defibrillator," Minimally Invasive Techniques; (Can be found on the World-Wide Web at http://chestioumal.chestpubs.org on May 6, 2013); dated Jan. 1993; 2 pages.
Frame et al., "Long-Term Stability of Defibrillation Thresholds with Intrapericardial Defibrillator Patches" Pacing and Clinical Electrophysiology, Jan. 1993, Part II, vol. 16, 6 pages.
Greatbatch Medical, OptiSeal Valved Peelable Introducer Brochure,, 2 pp. (Applicant points out, in accordance with MPEP 609.04(a), that the year of publication, 2010, is sufficiently earlier than the effective U.S. filing date so that the particular month of publication is not in issue).
Harman et al., "Differences in the Pathological Changes in Dog' Hearts After Defibrillation with Extrapericardial Paddles and Implanted Defibrillator Electrodes," Journal of Pacing and Clinical Electrophysiology, Feb. 1991; vol. 14; Part 2; 5 pages.
Karwande et al., Bilateral Anterior Thoracotomy for Automatic Implantable Cardioverter Defibrillator Placement in Patients with Previous Sternotomy, The Annals of Thoracic Surgery, Oct. 1992; 54(4); 3 pages.
Lawrie et al., "Right Mini-Thoracotomy: An Adjunct to Left Subcostal Automatic Implantable Cardioverter Defibrillator Implantation," The Annals of Thoracic Surgery; May 1989; 47; 4 pages.
Lemmer, "Defibrillator Patch Constriction, Letter to the Editor," The Annals of Thoracic Surgery, 1996 (Applicant points out, in accordance with MPEP 609.04(a), that the year of publication, 1996, is sufficiently earlier than the effective U.S. filing date so that the particular month of publication is not in issue), 1 page.
Medtronic, Inc. 6996SQ Subcutanesous, Unipolar Lead with Defibrillation Coil Electrode, Technical Manual, 2012 (Applicant points out, in accordance with MPEP 609.04(a), that the year of publication, 2012, is sufficiently earlier than the effective U.S. filing date so that the particular month of publication is not in issue) 22 pages.
Medtronic, Inc. 6996T Tunneling Tool, Technical Manual, 2011 ((Applicant points out, in accordance with MPEP 609.04(a), that the year of publication, 2011, is sufficiently earlier than the effective U.S. filing date so that the particular month of publication is not in issue)12 pages.
Mitchell et al., "Experience with an Implantable Tiered Therapy Device Incorporating Antitachycardia Pacing and Cardioverter/ Defibrillator Therapy," Thoracic and Cardiovascular Surgery, Abstract Only, Mar. 1993, 1 page.
Molina et al, "An Epicardial Subxiphoid Implantable Defibrillator Lead: Superior Effectiveness After Failure of Stndard Implants", From the Department of Surgery, Division of Cardiovascular and Thoracic Surgery and the Department of Medicine, Cardiac Arrhythmia Center, University of Minnesota Medical School, Minneapolis, Minnesota, Pace, vol. 27, Nov. 2004, 7 pages.
Obadia et al., "New Approach for Implantation of Automatic Defibrillators Using Videothoracoscopy," Journal Ann Cardiol Angeiol (Paris); Sep. 1994; 43 (7) Abstract Only, 1 page.
Obadia et al., "Thorasoscopic Approach to Implantable Cardioverter Defibrillator Patch Electrode Implantation," Pacing and Clinical Electrophysiology: Jun. 1996; vol. 19; 6 pages.
Pebax Product Brochure, 14 pages and can be found on-line at http://www.pebax.com/export/sites/pebax/content/medias/downloads/literature/pebax-product-rang-brouchure.pdf, Accessed Feb. 28, 2014, 14 pages.
Piccione et al., "Erosion of Extrapericardial Implantable Cardioverter Defibrillator Patch Through the Gastic Funds with Fistulous Tract Information," Cardiology in Review, Nov./Dec. 2006; 14, e21-e23 pages.
Prosecution History from U.S. Appl. No. 14/193,573, dated May 2, 2014 through Jul. 3, 2020, 195 pp.
Prosecution History from U.S. Appl. No. 14/193,634 dated May 16, 2016 through Jul. 8, 2020, 355 pp.
Prosecution History from U.S. Appl. No. 14/196,298, dated Jul. 16, 2015 through Sep. 3, 2019, 278 pp.
Prosecution History from U.S. Appl. No. 14/196,443, dated Mar. 4, 2014 through Dec. 9, 2016, 109 pp.
Prosecution History from U.S. Appl. No. 14/962,485, dated Jul. 13, 2017 through Apr. 1, 2021, 247 pp.
Prosecution History from U.S. Appl. No. 14/962,541, dated Jan. 5, 2018 through Oct. 24, 2020, 198 pp.
Prosecution History from U.S. Appl. No. 14/973,800 dated Sep. 19, 2017 through Apr. 17, 2019, 95 pp.
Quigley et al., "Migration of an Automatic Implantable Cardioverter-Defibrillator Patch Causing Massive Hemothorax," Journal Texas Heart Institute, Nov. 1, 1996; vol. 23, 4 pages.
Seifert et al., "Open Channel Implant Tools", Chinese Patent Application No. 201480072593.0, Third Office Action Mailed Mar. 29, 2019, 5 pages.
Shapira et al., A Simplified Method for Implantation of Automatic Cardioverter Defibrillator in Patients with Previous Cardiac Surgery, Pacing and Clinical Electrophysiology, Part 1, Jan. 1996, vol. 16; 6 pages.
Steinke et al., Subepicardial Infarction, Myocardial Impression, and Ventricular Penetration by Sutureless Electrode and Leads, Chest; 70: Jul. 1, 1976, 2 pages.
Tung et al., "Minimal Invasive Extra Cardiac Placement of High Voltage Defibrillator Leads", Poster 3; S200 Abstract, P0-3-4; St. Paul Hospital, Vancouver, British Columbia, Canada, Oct. 2007, 1 pages.
U.S. Appl. No. 17/062,183, filed Oct. 2, 2020, naming inventors Seifert et al.
Vyhmeister et al., "Simple Approach for Extrapericardial Placement of Defibrillator Patches via Median Sternotomy," The Annals of Thoracic Surgery; Dec. 1994; 57: 4 pages.
Response to Office Action dated Aug. 16, 2023 from U.S. Appl. No. 17/062,183, filed Nov. 15, 2023, 10 pp.
Office Action from U.S. App. No. 17/062,183 dated Aug. 16, 2023, 18 pp.
Advisory Action from U.S. Appl. No. 17/062,183 dated Mar. 28, 2024, 2 pp.
Final Office Action from U.S. Appl. No. 17/062,183 dated Jan. 17, 2024, 13 pp.
Response to Final Office Action dated Jan. 17, 2024 from U.S. Appl. No. 17/062,183, filed Mar. 14, 2024, 10 pp.
Office Action from U.S. Appl. No. 17/062,183 dated Jun. 21, 2024, 13 pp.

\* cited by examiner

SECTION A-A

EXTRAVASCULAR IMPLANT TOOLS UTILIZING A BORE-IN MECHANISM AND IMPLANT TECHNIQUES USING SUCH TOOLS

This application is a continuation of U.S. patent application Ser. No. 14/962,485, filed on Dec. 8, 2015, which claims the benefit of U.S. Provisional Patent Application No. 62/089,489, filed on Dec. 9, 2014. The entire content of each of these applications is incorporated herein by reference.

TECHNICAL HUD

The present disclosure relates to implant tools and techniques for implanting implantable medical leads or other implantable components in extravascular locations.

BACKGROUND

Implantable cardiac defibrillator (ICD) systems are used to deliver high energy electrical pulses or shocks to a patient's heart to terminate life threatening arrhythmias, such as ventricular fibrillation. Traditional ICD systems include a housing that encloses a pulse generator and other electronics of the ICD and is implanted subcutaneously in the chest of the patient. The ICD is connected to one or more implantable medical electrical leads that are implanted within the heart, referred to herein as transvenous leads.

Traditional ICD systems that utilize transvenous leads may not be the preferable ICD system for all patients. For example, some patients with difficult vascular access precludes placement of transvenous leads. As another example, children and other younger patients may also be candidates for non-transvenous ICD systems. Moreover, transvenous leads may become fibrosed in the heart over time, making lead revision and extraction procedures challenging.

SUMMARY

An extravascular ICD system may be preferred for some patients. An extravascular ICD system includes a lead (or leads) that are implanted extravascularly in the patient, e.g., outside and/or exclusive of the heart. As such, the extravascular ICD may eliminate the need to implant transvenous leads within the heart. Instead, the lead(s) may be implanted subcutaneously, substernally, or in other extravascular locations.

This application presents extravascular implant tools that utilize a bore-in mechanism to safely traverse the diaphragmatic attachments to access the substernal space. As will be described herein, using the bore-in mechanism may allow the implant tool to traverse the diaphragmatic attachments while controlling momentum of the implant tool after the traversal of the attachments. In this manner, the implant tool allows traversing of the diaphragmatic attachments with a reduced likelihood of damage to surrounding organs.

For example, this application provides an implant tool for implanting an implantable medical lead, implantable catheter or other implantable component within a patient. The implant tool includes an open channel delivery tool having a handle and a shaft adjacent the handle. The shaft has a proximal end, a distal end, and an open channel that extends from near the proximal end to the distal end. The implant tool also includes a bore-in mechanism configured to interact with the open channel delivery tool. In one example, the bore-in mechanism includes a handle and a helix extending from the handle, the handle and the helix forming a lumen that extends through the handle and the helix and is configured to receive the shaft of the open channel delivery tool. In another example, the bore-in mechanism comprises a handle and a screw extending from the handle, wherein the open channel of the delivery tool is sized to receive the screw of the bore-in mechanism.

In another example, this application provides a method for implanting a medical lead, a catheter or other implantable component, the method comprising screwing a bore-in mechanism into the diaphragmatic attachments of a patient, placing a shall of an open channel delivery tool adjacent to the bore-in mechanism, simultaneously pulling the bore-in mechanism while pushing the open channel delivery tool to traverse the diaphragmatic attachments.

In a further example, this application provides an implant tool for implanting an implantable medical lead, implantable catheter or other implantable component within a patient. The implant tool includes a bore-in mechanism having a handle and a helix extending from the handle. The handle and the helix form a lumen that extends through the handle and the helix. The implant tool also includes a tunneling tool that includes a shaft configured to be placed through the lumen of the bore-in mechanism. In one example, the tunneling tool comprises an open channel delivery tool that includes a handle and a shall adjacent the handle, the shaft having a proximal end, a distal end, and an open channel that extends from near the proximal end to the distal end. In another example, the tunneling tool comprises a rod and a sheath configured to be placed over the rod.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
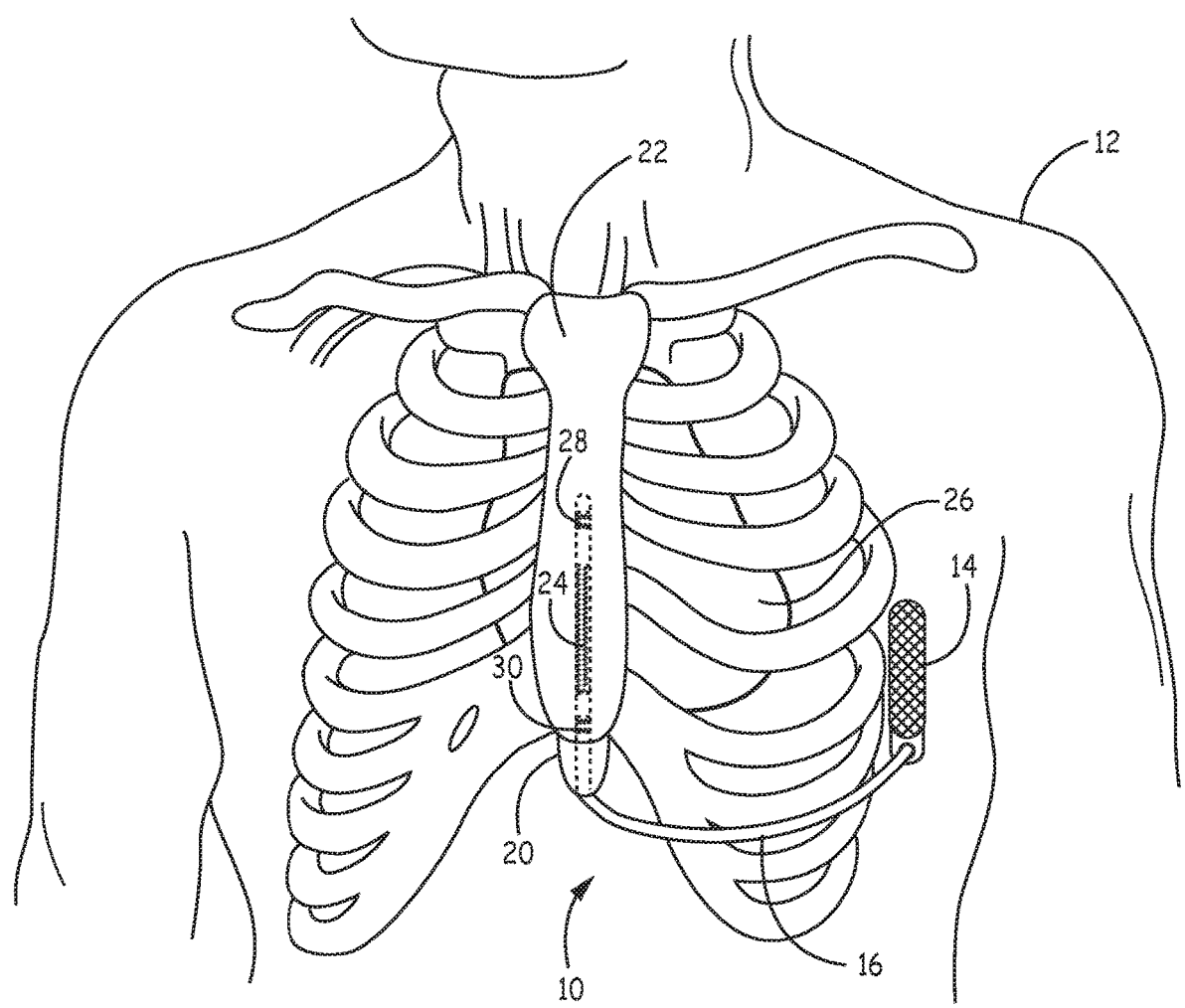
FIG. 1A is a front view of an example extravascular ICD system implanted within a patient.
Figure 1B:
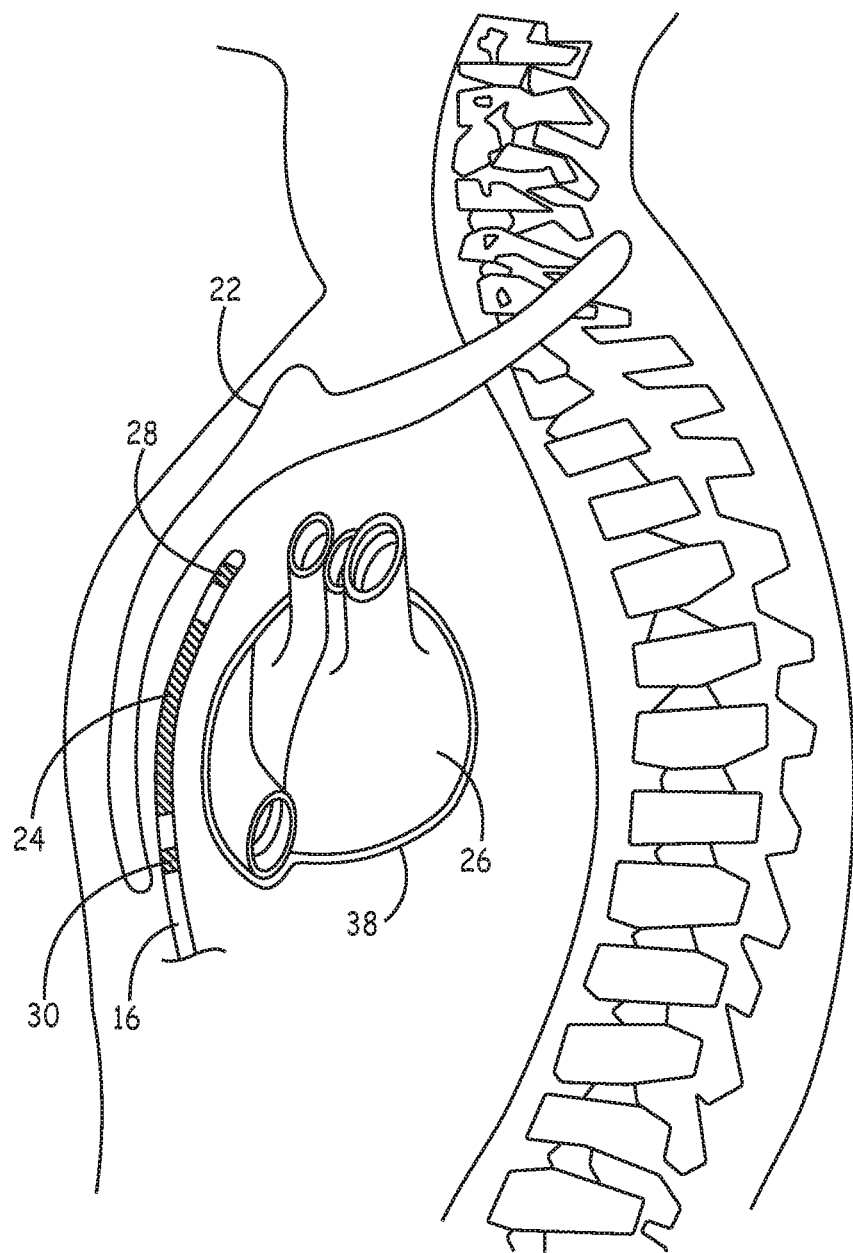
FIG. 1B is a side view of the extravascular ICD system implanted within the patient.
Figure 1C:
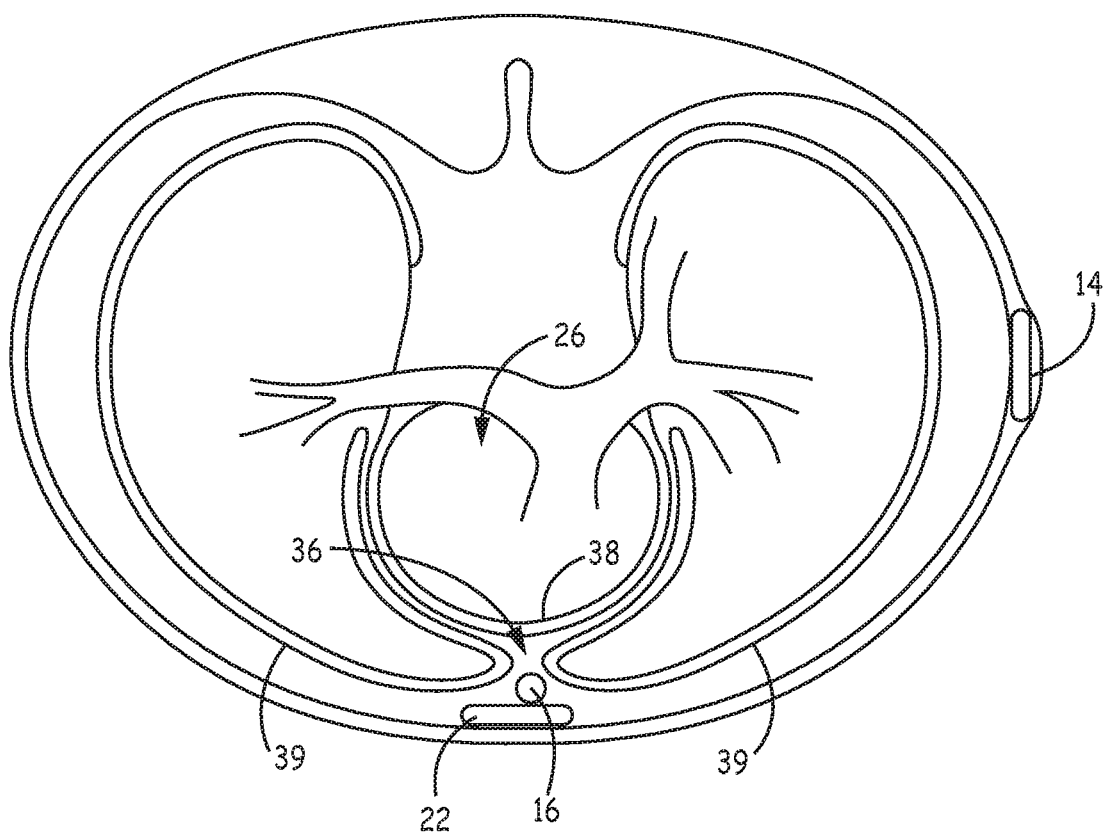
FIG. 1C is a transverse view of the extravascular ICD system implanted within the patient.

FIGS. 1A-C are conceptual diagrams of an extravascular ICD system 10 implanted within a patient 12. FIG. 1A is a front view of ICD system 10 implanted within patient 12. FIG. 1B is a side view of ICD system 10 implanted within patient 12. FIG. 1C is a transverse view of ICD system 10 implanted within patient 12. ICD system 10 includes an ICD 14 connected to a medical electrical lead 16. FIGS. 1A-C are described in the context of an ICD system capable of providing defibrillation and/or cardioversion shocks and, in some instances, pacing pulses. However, the techniques of this disclosure may also be used in the context of other implantable medical devices configured to provide other electrical stimulation therapies to the heart.

ICD 14 may include a housing that forms a hermetic seal that protects components of ICD 14. The housing of ICD 14 may be formed of a conductive material, such as titanium, or of a combination of conductive and non-conductive materials. The conductive material of the housing functions as a housing electrode. ICD 14 may also include a connector assembly (also referred to as a connector block or header) that includes electrical feedthroughs through which electrical connections are made between lead 16 and electronic components included within the housing. The housing may house one or more processors, memories, transmitters, receivers, sensors, sensing circuitry, therapy circuitry, power sources and other appropriate components.

ICD 14 is configured to be implanted in a patient, such as patient 12. ICD 14 is implanted extra-thoracically (e.g., subcutaneously or submuscularly) on the left midaxillary of patient 12. ICD 14 is on the left side of patient 12 outside the ribcage. ICD 14 may, in some instances, be implanted between the left posterior axillary line and the left anterior axillary line of patient 12. ICD 14 may, however, be implanted at other subcutaneous locations on patient 12 such as at a pectoral location or abdominal location.

Lead 16 includes an elongated lead body having a proximal end that includes a connector (not shown) configured to be connected to ICD 14 and a distal portion that includes electrodes 24, 28, and 30. The implant tools and techniques of this disclosure may be used to implant lead 16 as described herein. Lead 16 extends extra-thoracically, e.g., under skin and outside the ribcage (subcutaneously or submuscularly) from ICD 14 toward a center of the torso of patient 12, e.g., toward xiphoid process 20 of patient 12. At a location near the center of the torso, lead 16 bends or turns and extends superior intra-thoracically in a substernal location under/below sternum 22 and/or ribcage of the patient 12. In one example, the substernal location is substantially within anterior mediastinum 36 such that distal portion of lead 16 extends superior along the posterior side of the sternum within anterior mediastinum 36. Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), adipose tissue, some lymph vessels, lymph glands, substernal musculature (e.g., transverse thoracic muscle), the thymus gland, branches of the internal thoracic artery, and the internal thoracic vein. In one example, the distal portion of lead 16 may be implanted substantially within the loose connective tissue and/or substernal musculature of anterior mediastinum 36.

In other embodiments, the distal portion of lead 16 may be implanted in other intra-thoracic, non-vascular, extra-pericardial locations, including the gap, tissue, or other anatomical features around the perimeter of and adjacent to, but not attached to, the pericardium or other portion of heart 26 and not outside sternum 22 or ribcage (e.g., within the pleural cavity). As such, lead 16 may be implanted anywhere within the "substernal location" defined by the undersurface between the sternum and/or ribcage and the body cavity but not including the pericardium or other portion of heart 26. The substernal location may alternatively be referred to by the terms "retrosternal space" or "mediastinum" or "infrasternal" as is known to those skilled in the art and includes the anterior mediastinum 36. The substernal location may also include the anatomical region described in Baudoin, Y. P., et al., entitled "The superior epigastric artery does not pass through Larrey's space (trigonum stemocostale)." Surg. Radiol. Anat. 25.3-4 (2003): 259-62. In other words, the distal portion of lead 16 may be implanted in the region around the outer surface of heart 26, but not attached to heart 26.

The distal portion of lead 16 may be implanted substantially within anterior mediastinum 36 such that electrodes 24, 28, and 30 are located near a ventricle of heart 26. For instance, lead 16 may be implanted within anterior mediastinum 36 such that electrode 24 is located over a cardiac silhouette of one or both ventricles as observed via an anterior-posterior (AP) fluoroscopic view of heart 26. In one example, lead 16 may be implanted such that a therapy vector from electrode 24 to a housing electrode of ICD 14 is substantially across the ventricles of heart 26. The therapy vector may be viewed as a line that extends from a point on electrode 24, e.g., center of electrode 24, to a point on the housing electrode of ICD 14, e.g., center of the housing electrode. However, lead 16 may be positioned at other locations as long as the therapy vector between electrode 24 and the housing electrode is capable of defibrillating heart 26.

In the example illustrated in FIGS. 1A-C, lead 16 is located substantially centered under sternum 22. In other instances, however, lead 16 may be implanted such that it is offset laterally from the center of sternum 22. In some instances, lead 16 may extend laterally enough such that all or a portion of lead 16 is underneath/below the ribcage in addition to or instead of sternum 22.

The elongated lead body of lead 16 contains one or more elongated electrical conductors (not illustrated) that extend within the lead body from the connector at the proximal lead end to electrodes 24, 28, and 30 located along the distal portion of lead 16. The elongated lead body may have a generally uniform shape along the length of the lead body. In one example, the elongated lead body may have a generally tubular or cylindrical shape along the length of the lead body. The elongated lead body may have a diameter of between 3 and 9 French (Fr) in some instances. However, lead bodies of less than 3 Fr and more than 9 Fr may also be utilized. In another example, the distal portion (or all of) the elongated lead body may have a flat, ribbon or paddle shape. In this instance, the width across the flat portion of the flat, ribbon or paddle shape may be between 1 and 3.5 mm. Other lead body designs may be used without departing from the scope of this disclosure. The lead body of lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead body of lead 16 may engage with respective ones of electrodes 24, 28, and 30. In one example, each of electrodes 24, 28, and 30 is electrically coupled to a respective conductor within the lead body. The respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 24, 28, and 30 and transmit sensed electrical signals from one or more of electrodes 24, 28, and 30 to the sensing module within ICD 14.

Defibrillation electrode 24 is illustrated in FIG. 1 as being an elongated coil electrode. Defibrillation electrode 24 may vary in length depending on a number of variables. Defibrillation electrode 24 may, in one example, have a length between approximately 5-10 centimeters (cm). However, defibrillation electrode 24 may have a length less than 5 cm and greater than 10 cm in other embodiments. Another example, defibrillation electrode 24 may have a length between approximately 2-16 cm.

In other embodiments, however, defibrillation electrode 24 may be a flat ribbon electrode, paddle electrode, braided or woven electrode, mesh electrode, segmented electrode, directional electrode, patch electrode or other type of electrode besides an elongated coil electrode. In one example, defibrillation electrode 24 may be formed of a first segment and a second segment separated by a distance and having an electrode or a pair of electrodes (such as electrode 28 and/or 30 described below) located between the first and second defibrillation electrode segments. In one example, the segments may be coupled to the same conductor within the lead body such that the first and second segments function as a single defibrillation electrode. In other embodiments, defibrillation lead 16 may include more than one defibrillation electrode. For example, the first and second segments described above may be coupled to different conductors within the lead body such that the first and second segments function as separate defibrillation electrodes along the distal portion of lead 16. As another example, defibrillation lead 16 may include a second defibrillation electrode (e.g., second elongated coil electrode) near a proximal end of lead 16 or near a middle portion of lead 16.

Lead 16 also includes electrodes 28 and 30 located along the distal portion of lead 16. In the example illustrated in FIGS. 1A-C, electrodes 28 and 30 are separated from one another by defibrillation electrode 24. In other examples, however, electrodes 28 and 30 may be both distal of defibrillation electrode 24 or both proximal of defibrillation electrode 24. In instances in which defibrillation electrode 24 is a segmented electrode with two defibrillation segments, electrodes 28 and 30 may be located between the two segments. Alternatively, one of electrodes 28 and 30 may be located between the two segments with the other electrode located proximal or distal to defibrillation electrode 24. Electrodes 28 and 30 may comprise ring electrodes, short coil electrodes, hemispherical electrodes, segmented electrodes, directional electrodes, or the like. Electrodes 28 and 30 of lead 16 may have substantially the same outer diameter as the lead body. In one example, electrodes 28 and 30 may have surface areas between 1.6-55 mm². Electrodes 28 and 30 may, in some instances, have relatively the same surface area or different surface areas. Depending on the configuration of lead 16, electrodes 28 and 30 may be spaced apart by the length of defibrillation electrode 24 plus some insulated length on each side of defibrillation electrode, e.g., approximately 2-16 cm. In other instances, such as when electrodes 28 and 30 are between a segmented defibrillation electrode, the electrode spacing may be smaller, e.g., less than 2 cm or less the 1 cm. The example dimensions provided above are exemplary in nature and should not be considered limiting of the embodiments described herein. In other examples, lead 16 may include a single pace/sense electrode or more than two pace/sense electrodes.

In some instances, electrodes 28 and 30 of lead 16 may be shaped, oriented, designed or otherwise configured to reduce extracardiac stimulation. For example, electrodes 28 and 30 of lead 16 may be shaped, oriented, designed or otherwise configured to focus, direct or point electrodes 28 and 30 toward heart 26. In this manner, pacing pulses delivered via lead 16 are directed toward heart 26 and not outward toward skeletal muscle. For example, electrodes 28 and 30 of lead 16 may be partially coated or masked with a polymer (e.g., polyurethane) or another coating material (e.g., tantalum pentoxide) on one side or in different regions so as to direct the pacing signal toward heart 26 and not outward toward skeletal muscle.

ICD 14 may obtain sensed electrical signals corresponding with electrical activity of heart 26 via a combination of sensing vectors that include combinations of electrodes 28 and/or 30 and the housing electrode of LCD 14. For example, ICD 14 may obtain electrical signals sensed using a sensing vector between electrodes 28 and 30, obtain electrical signals sensed using a sensing vector between electrode 28 and the conductive housing electrode of ICD 14, obtain electrical signals sensed using a sensing vector between electrode 30 and the conductive housing electrode of LCD 14, or a combination thereof. In some instances, ICD 14 may even obtain sensed electrical signals using a sensing vector that includes defibrillation electrode 24.

ICD 14 analyzes the sensed electrical signals obtained from one or more of the sensing vectors of lead 16 to monitor for tachyarrhythmia, such as ventricular tachycardia or ventricular fibrillation. ICD 14 generates and delivers substernal electrical stimulation therapy, e.g., ATP, cardioversion or defibrillation shocks, and/or post-shock pacing in response to detecting tachycardia (e.g., VT or VF). In some instances, ICD 14 may generate and deliver bradycardia pacing in addition to ATP, cardioversion or defibrillation shocks, and/or post-shock pacing.

In the example illustrated in FIG. 1, system 10 is an ICD system that provides cardioversion/defibrillation and/or pacing therapy. However, the implant tools and techniques may be utilized to implant other types of implantable medical leads, catheters (e.g., drug delivery catheters), or other implantable component or assembly. In addition, it should be noted that system 10 may not be limited to treatment of a human patient. In alternative examples, system 10 may be implemented in non-human patients, e.g., primates, canines, equines, pigs, ovines, bovines, and felines. These other animals may undergo clinical or research therapies that may benefit from the subject matter of this disclosure.

Figure 2:
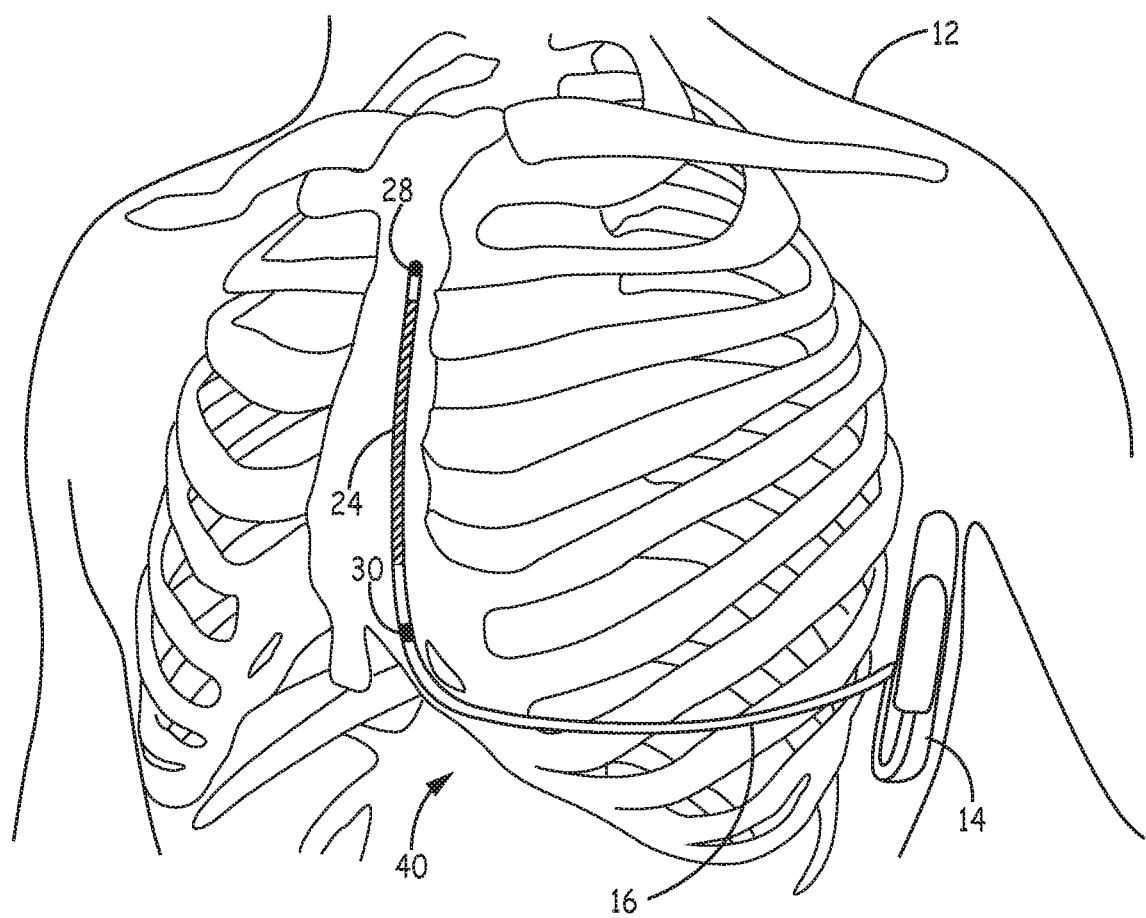
FIG. 2 is a conceptual diagram of another example extravascular ICD system implanted extrathoracically within a patient.

FIG. 2 is a conceptual diagram of another example extravascular ICD system 40 implanted extra-thoracically within patient 12. In the example illustrated in FIG. 2, extravascular ICD system 40 is an implanted subcutaneous ICD system. ICD system 40 conforms substantially to ICD system 10 of FIGS. 1A-1C except that the distal portion of lead 16 is implanted extra-thoracically under the skin and outside the sternum and/or the ribcage (subcutaneously or submuscularly). In this case, ICD 14 may include additional components necessary to generate high voltage shocks at energies greater than ICD system 10, e.g., up to 80 J instead of 35-60 J.

Figure 3:
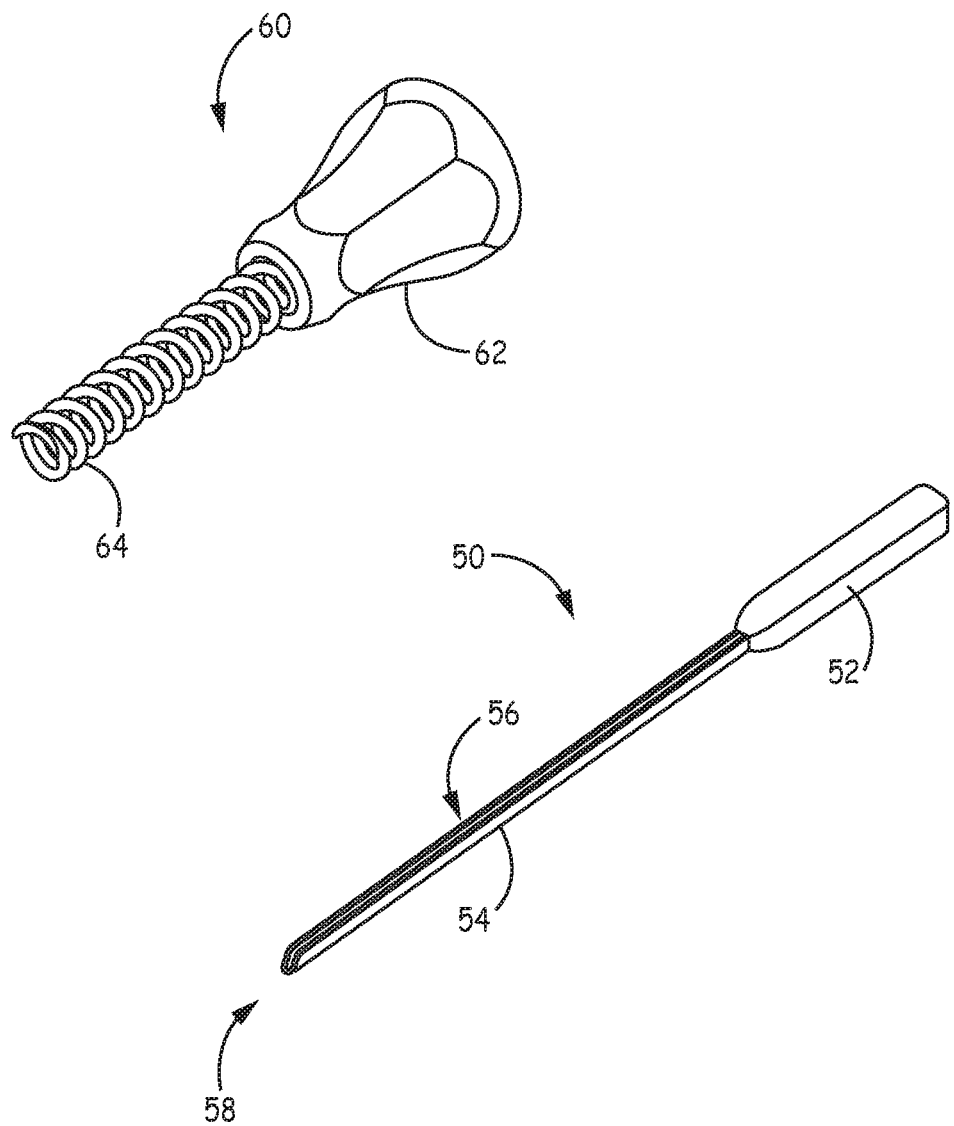
FIG. 3 is a conceptual diagram illustrating an example implant tool that includes an open channel delivery tool that is used in conjunction with a bore-in mechanism to implant a component extravascularly.

FIG. 3 is a conceptual diagram illustrating an example implant tool that includes an open channel delivery tool 50 and a bore-in mechanism 60. Open channel delivery tool 50, which is illustrated in further detail in FIGS. 5A-5C, includes a handle 52 and an elongate shaft 54 adjacent to handle 52. Shaft 54 defines an open channel 56 that extends from handle 52 to a distal end 58. Open channel 56 may extend the entire length of shaft 54 from handle 52 to distal end 58 in one embodiment.

Figure 4A:
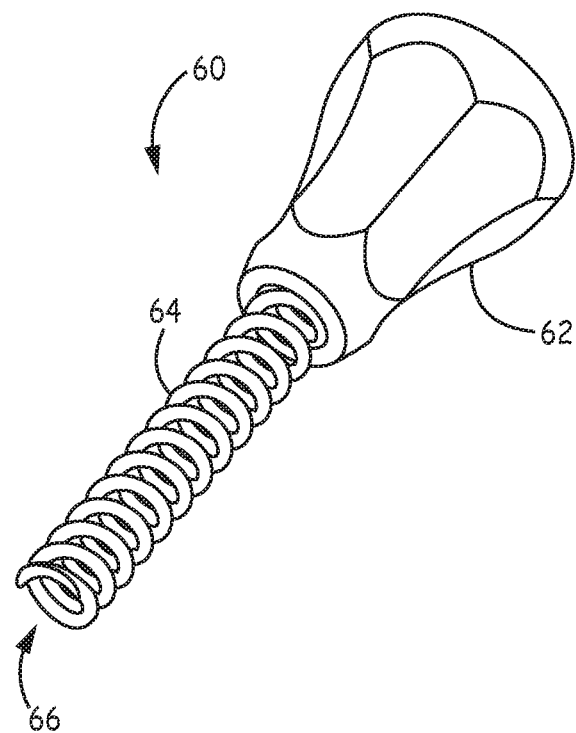
FIG. 4A illustrates an angled view of the bore-in mechanism of the implant tool of FIG. 3.
Figure 4B:
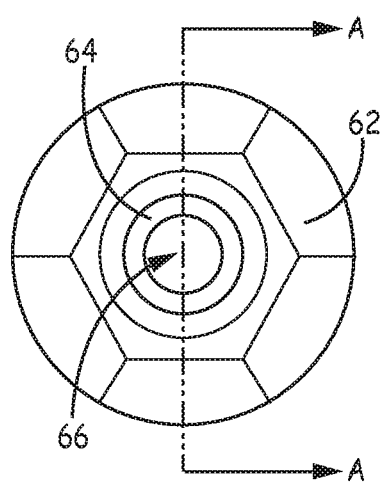
FIG. 4B illustrates a front view of the bore-in mechanism of the implant tool of FIG. 3.
Figure 4C:
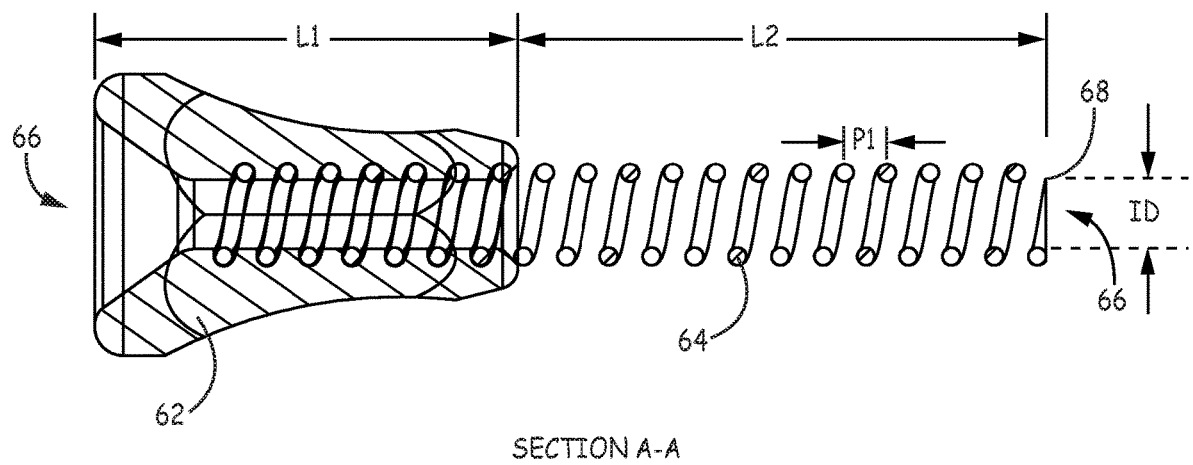
FIG. 4C illustrates a longitudinal side view of the bore-in mechanism of the implant tool of FIG. 3 taken from A-A' in FIG. 4B.

Bore-in mechanism 60, which is illustrated in further detail in FIGS. 4A-4C, includes a handle 62 and a helix 64. FIG. 4A illustrates an angled view of bore-in mechanism 60. FIG. 4B illustrates a front view of bore-in mechanism 60. FIG. 4C illustrates a longitudinal side view of bore-in mechanism 60 taken from A-A' in FIG. 4B.

Handle 62 and helix 64 form a lumen 66 that extends the entire length of bore-in mechanism 60. Helix 64 may be constructed of a metal, metal alloy, or rigid polymer. In one example, helix 64 may be formed from a wire. The wire may be of any of a variety of diameters. In one example, the wire diameter may be between approximately 0.035-0.100 inches. However, wires of other diameters may also be used without departing from the scope of this disclosure.

Helix 64 extends from handle 62 for a length L2 from handle to a distal end 68. Distal end 68 of helix 64 may be ground or otherwise formed to have sharp tip. Length L2 may be between approximately 1.5-3.5 inches. However, the actual length of helix 64 may be slightly longer than L2 as helix 64 may extend within handle 62 (as illustrated in FIG. 4C to aid in coupling of helix 64 to handle 64. Helix 64 has a pitch (P1). The pitch, which is the width of one complete helix turn, may be 0.1-0.3 inches. However, pitches smaller than 0.1 inches and larger than 0.3 inches may also be utilized.

Shaft 54 of open channel delivery tool 50 and bore-in mechanism 60 are sized such that shaft 54 may pass through lumen 66. Thus, the diameter of lumen 66 (or the inner diameter (ID) of helix 64) may be formed to accommodate shaft 54 of open channel delivery tool 50. The ID of helix 64 may, for example, be between approximately 0.15-0.50 inches. However, IDs of smaller than 0.15 inches and larger than 0.50 inches may also be utilized. The outer diameter (OD) of helix 64 will depend on the diameter of the wire or other material used to form helix 64.

Handle 62 may be constructed of metal, alloy, polymer, or other material or combination of materials. Handle 62 may be sized and shaped to fit within a hand and be ergonomically comfortable. Handle 62 may, for example, have a length between 1.25-4.0 inches. However, handle 62 may have lengths greater and less than this range without departing from the scope of this disclosure. Handle 62 of FIG. 3 and FIG. 4 is a six-sided handle. The handle may include more or fewer sides (e.g., 3-sided). In other instances, handle 62 may be completely smooth handle (e.g., cylindrical), may be a "T" handle, or other type of handle.

Figure 5A:
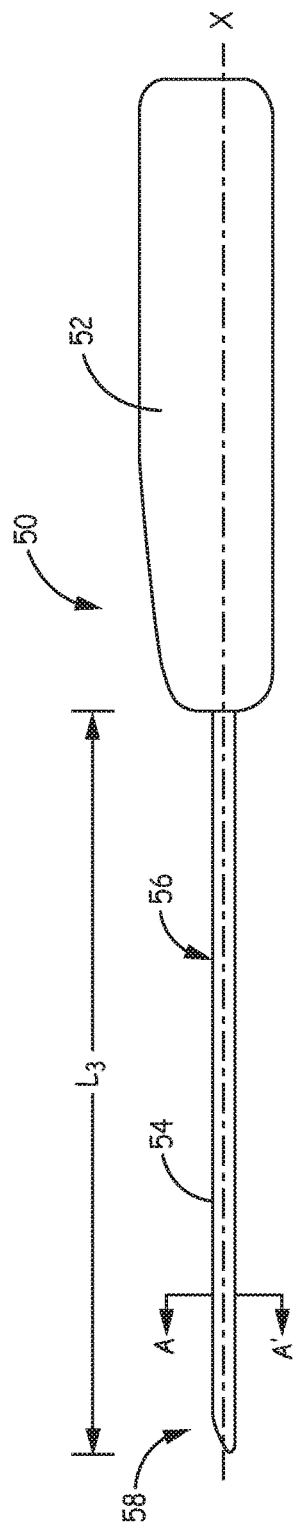
FIG. 5A illustrates a longitudinal side view of the open channel delivery tool of the implant tool of FIG. 3.
Figure 5B:
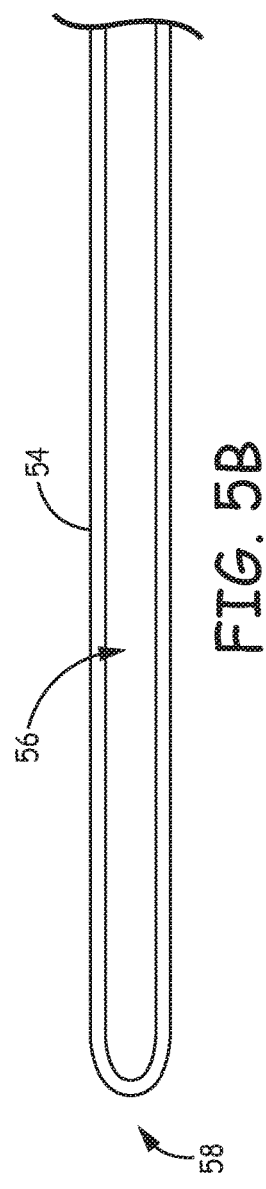
FIG. 5B illustrates a top view of a shaft of the open channel delivery tool of the implant tool of FIG. 3.
Figure 5C:
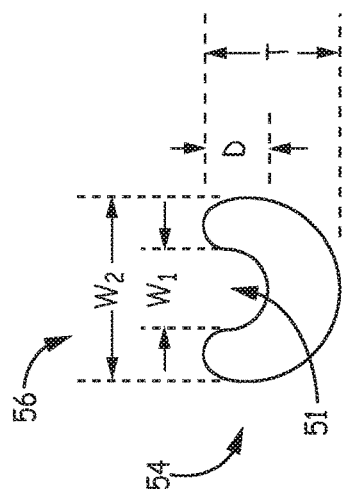
FIG. 5C illustrates a cross sectional view of a distal end of the open channel delivery tool of the implant tool of FIG. 3 taken from A-A' in FIG. 5A.

FIGS. 5A-C are conceptual drawings illustrating an example extravascular implant tool 30 for implanting a medical lead, such as lead 16 of FIGS. 1 and 2, a catheter, or other implantable component. FIG. 5A illustrates a longitudinal side view of open channel delivery tool 50. FIG. 5B illustrates a top view of a shaft of open channel delivery tool 50. FIG. 5C illustrates a cross sectional view of a distal end of open channel delivery tool 50 taken from A-A' in FIG. 5A. As will be described in further detail herein, open channel delivery tool 50 of FIGS. 5A-C may be particularly useful in implanting defibrillation lead 16 in patient 12 in a subcutaneous, substernal, or other extravascular location.

As described above, open channel delivery tool 50 includes a handle 52 and an elongate shaft 54 adjacent to handle 52, the shaft 54 defining an open channel 56 that extends from handle 52 to a distal end 58. Open channel 56 may extend the entire length of shaft 54 from handle 52 to distal end 58 in some embodiments. Shall 24 extends a length "L3" from handle 52 to distal end 58. The length L3 of shaft 54 may be determined based on the desired tunneling application. For example, shaft 54 may have a length between approximately 5 to 11 inches in some instances. However, other lengths may be appropriate for other desired applications.

Shaft 54 may have a relatively uniform thickness along the longitudinal length of shaft 54, e.g., along major axis "X" defined by open channel delivery tool 50. Alternatively, the thickness of the walls of shaft 54 may not be uniform along the length of shaft 54. For example, the walls of shall 54 may have an increased thickness toward distal end 58 compared to the proximal end of shaft 54. The increase in thickness toward distal end 58 may enable improved tunneling performance by increasing rigidness or stiffness at distal end 58 or by reducing interference with the tissue. Additionally, the increase thickness of distal end 58 may aid in shaping distal end to avoid coring, cutting, or puncturing of tissue, pleura, pericardium or other parts of patient 12. In other instances, distal end 58 and the proximal end near handle 52 of shaft 54 may have a greater thickness compared to the middle portion of shaft 54.

As illustrated in the cross sectional view of distal end 58 of shaft 54, taken perpendicular to the longitudinal length of shaft 54 from handle 52 to distal end 58 (e.g., orthogonal to the major axis X defined by open channel delivery tool 50), shaft 54 has a generally arc-shaped cross section that defines a generally arc-shaped open channel 56 (e.g., U-shaped and/or C-shaped). In other examples, however, the cross-section of shaft 54 and open channel 56 may be formed into any of a number of different shapes including, but not limited to, horseshoe-shape or other shape.

Open channel 56 has a depth, labeled "D" in FIG. 5C. Depth D of channel 56 may, in one example, be approximately equal to an outer diameter the lead. In further examples, the depth D of open channel 56 may be slightly larger than the outer diameter of the lead to provide some margin. In further instances, open channel 56 may be sized to account for the largest portion of the lead, such as a fixation mechanism (such as tines), an anchoring sleeve, a connector, or other portion of the lead, with or without margin. The margin may allow the user push the lead along open channel 56 without too much interference or friction.

Open channel 56 also includes a width, labeled "W1" in FIG. 5C. In one example, width W1 of open channel 56 is less than the outer diameter of the lead. In another example, width W1 of open channel 56 is approximately equal to the outer diameter of the lead such that when the implantable electrical lead 16 is placed within open channel 56 there is a slight interference fit. In a further example, width W1 of open channel 56 is greater than an outer diameter of the lead (e.g., the diameter of the lead plus a slight margin).

Shaft 54 may have the same cross section along the entire length of shaft 54. Alternatively, shaft 54 may have varying cross sections along portions of the length of shaft 54. For example, may have a more open cross-section, e.g., a U-shaped cross-section toward a proximal end of shaft 54 and a C-shaped cross-section along the mid and distal sections of the shaft 54. Other varying cross-sections may be utilized without departing from the scope of this disclosure. Shaft 54 may have a total cross-sectional thickness (T) of between approximately 0.080-0.450 inches and a total width (W2) of approximately 0.080-0.450 inches.

In the examples described above, open channel delivery tool 50 may be used to implant a particular sized lead such that a different implant tool (e.g., having a different sized open channel 56) may be selected depending on the size of the lead to be implanted, which may range from 2 French to 11 French. In further examples, a single open channel delivery tool 50 may be designed to deliver leads having a variety of different diameters. In this case, the depth D and width W of open channel 56 may be sized for delivery of the largest diameter lead for which tool 50 is designed.

Shaft 54 may have a relatively uniform thickness along the sides and bottom of the body of shaft 54. In other words, the walls along the sides and bottom of shaft 54 may all have about the same thickness. In another example, however, shaft 54 may have thicker walls along the sides of shaft 54 forming open channel 56 than along the bottom of shaft 54.

Elongate shaft 54 of open channel delivery tool 50 is formed such that it is stiff enough to be capable of being pushed through the tissue, muscle or other structure to form a path through the body. Shaft 54 may be made of a metal, polymer, or other material or combination of materials, e.g., metal and polymer. Such a tool could be extruded, molded, or inserted as part of a manufacturing process and would provide additional stiffness and malleability to the implant tool. In some instances, such as when shaft 54 is made of metal or a combination of metal and polymer, shaft 54 may be malleable. In other instances, shaft 54 of tool 50 may not be malleable, e.g., when shaft 54 is made of a molded polymer. In further instances, the implant tool may include a pre-formed or pre-shaped shaft 54. In this case, shaft 54 may be somewhat flexible while still being stiff enough to tunnel through tissue. The flexibility may allow a user to manipulate the tool slightly to control direction (e.g., steer) of the tunnel.

Handle 52 of open channel delivery tool 50 may also be made of a metal, alloy, polymer, or other material or combination of materials. Handle 52 and elongate shaft 54 may, in some instances, be constructed of the same material. For example, open channel delivery tool 50 may be formed of a single, unitary piece of material, such as metal or rigid polymer. In other instances, handle 52 and elongate shaft 54 may be constructed of different materials. In this case, handle 52 and shaft 54 may be formed of separate components that are attached together to form open channel delivery tool 50, e.g., via a two piece construction. For example, handle 52 may be made of polymer and shaft 54 may be made of metal and attached to handle 52 to form open channel delivery tool 50. Example metals or alloys from which handle 52 or shaft 54 may be constructed include, but are not limited to, stainless steel, titanium, titanium alloys, nickel-cobalt, and nickel-cobalt alloys. Example polymers may include, but are not limited to, acetal resin (e.g., DELRIN®), polyether ether ketone (PEEK), polycarbonate, polypropylene composites, and liquid-crystal polymer (LCP). In addition, lubricious fillers and coatings may be used to improve lubricity during tunneling and lead insertion. Such additives or coatings include, but are not limited to, siloxane, PTFE, and Foster ProPell™. Example radiopaque additives may include, without limitation, BaSO4, WC, and Bi2O3.

Distal end 58 of shaft 54 may be shaped to aid in tunneling through tissue or muscle. For example, distal end 58 of the shaft 54 may be tapered, angled, blunt, rounded, pointed, bent or otherwise shaped to enable a user to tunnel through tissue, ligaments, muscle or other structure without excess damage to surrounding tissue, piercing through the skin, or coring of the tissue.

Open channel delivery tool 50 and bore-in tool 60 may be used in conjunction with one another to safely traverse the diaphragmatic attachments. In one example, open channel delivery tool 50 and bore-in tool 60 may be used together to access the substernal space. As will be described below, using the tools in conjunction with one another may allow traversing the diaphragmatic attachments while controlling momentum of the shaft 54 of delivery tool 50 after the traversal of the attachments. In this manner, the implant tool allows traversing of the diaphragmatic attachments with a reduced likelihood of damage to surrounding organs.

Initially, an implanter or other user grips handle 62 and screws distal end 68 of helix 64 of bore-in tool 60 until the helix is firmly embedded into the diaphragmatic attachments near a center of the torso of patient 12 (e.g., just below the xiphoid process). In one example, distal end 68 of helix 64 does not traverse the diaphragmatic attachments. In another example, distal end 68 of helix 64 does traverse the diaphragmatic attachments.

After embedding helix 64 of bore-in mechanism 60 into the diaphragmatic attachments, distal end 58 of shaft 54 of open channel delivery tool 50 is inserted within lumen 66 of bore-in mechanism 60. In particular, distal end 58 of shaft 54 is placed within lumen 66 near handle 62 and advanced toward distal end 68 of helix 64. Bore-in mechanism 60 is pulled away from patient 12 while shaft 54 of open channel delivery tool 50 is advanced toward patient 12. By pulling bore-in mechanism 60 away from patient 12, the diaphragmatic attachments are pulled slightly away from chest cavity providing additional space for the distal end 58 of shaft 54 of open channel delivery tool 50 after it traverses the diaphragmatic attachments. In this manner, the implant tool allows traversing of the diaphragmatic attachments with a reduced likelihood of damage to surrounding organs.

After traversing the diaphragmatic attachments with shaft 54 of open channel delivery tool 50, bore-in mechanism 60 may either be left in place or may be unscrewed from the diaphragmatic attachments and moved to the proximal end of shaft 54. Distal end 58 of shaft 54 may be tunneled along the posterior side of the sternum to a desired location. Once at the desired location, the user may deliver an implantable electrical lead, such as defibrillation lead 16 of FIG. 1, catheter or other implantable structure in the tunnel or path formed by open channel delivery tool 50 by pushing the defibrillation lead 16 through open channel 56 of shaft 54 and then removing tool 50 while leaving defibrillation lead 16 in the path created by the implant tool.

Delivery tool 50 may be used to form a subcutaneous tunnel lateral between the center of the torso of the patient to a pocket on the left side of the patient. Lead 16 may be advance along channel 56 and delivery tool 50 may be removed leaving the proximal portion of lead 16 in place along the lateral path. This may be done before or after the substernal tunneling. The connector of lead 16 may be connected to the ICD.

In other embodiments, bore-in mechanism 60 may be integrated within delivery tool 50. For example, bore-in mechanism 60 may be permanently mounted on delivery tool 50 and capable of sliding along shaft 54. In such a case, deliver tool 50 and/or bore-in mechanism 60 may include some sort of locking mechanism by which bore-in mechanism may be fixed at the distal end during the boring and traversing process and then unlocked and slid to the proximal end of shaft 54 during the tunneling process. Moreover, delivery tool 50 may include some sort of trigger or other actuation mechanism for controllably moving shaft 54 through the lumen of bore-in mechanism 60 to controllably traverse the diaphragmatic attachments. The trigger may, for example, move shaft 54 a fixed distance relative to bore-in mechanism each time the trigger is actuated.

Additionally, although the implant tool of FIG. 3 utilizes an open channel delivery tool in conjunction with bore-in element 60, the implant tool of FIG. 3 and/or the procedure described above can be performed using a more conventional tunneling tool (e.g., metal or polymer rod) and sheath. Example rods and sheaths include, but are not limited to, the Medtronic™ 6996T tunneling tool, Emblem™ S-ICD Subcutaneous Electrode Insertion Tool (Model 4711) distributed by Boston Scientific™, and the OptiSeal™ Valved Peelable Introducer distributed by Greatbatch™ Medical. In yet another embodiment, bore-in mechanism 60 may be used with other lead implant techniques, such as over the wire implant techniques. In this example, bore-in mechanism 60 may be constructed such that lumen 66 is sized to receive a guide wire. Bore-in mechanism 60 is screwed through the diaphragmatic attachments and the guide wire is routed through lumen 60 into the substernal space. Once the guide wire is placed within the substernal space, the bore-in mechanism is removed. An introducer or other vascular access device may dilate the opening through the diaphragmatic attachments. A lead may then be placed using an over-the-wire technique.

Figure 6:
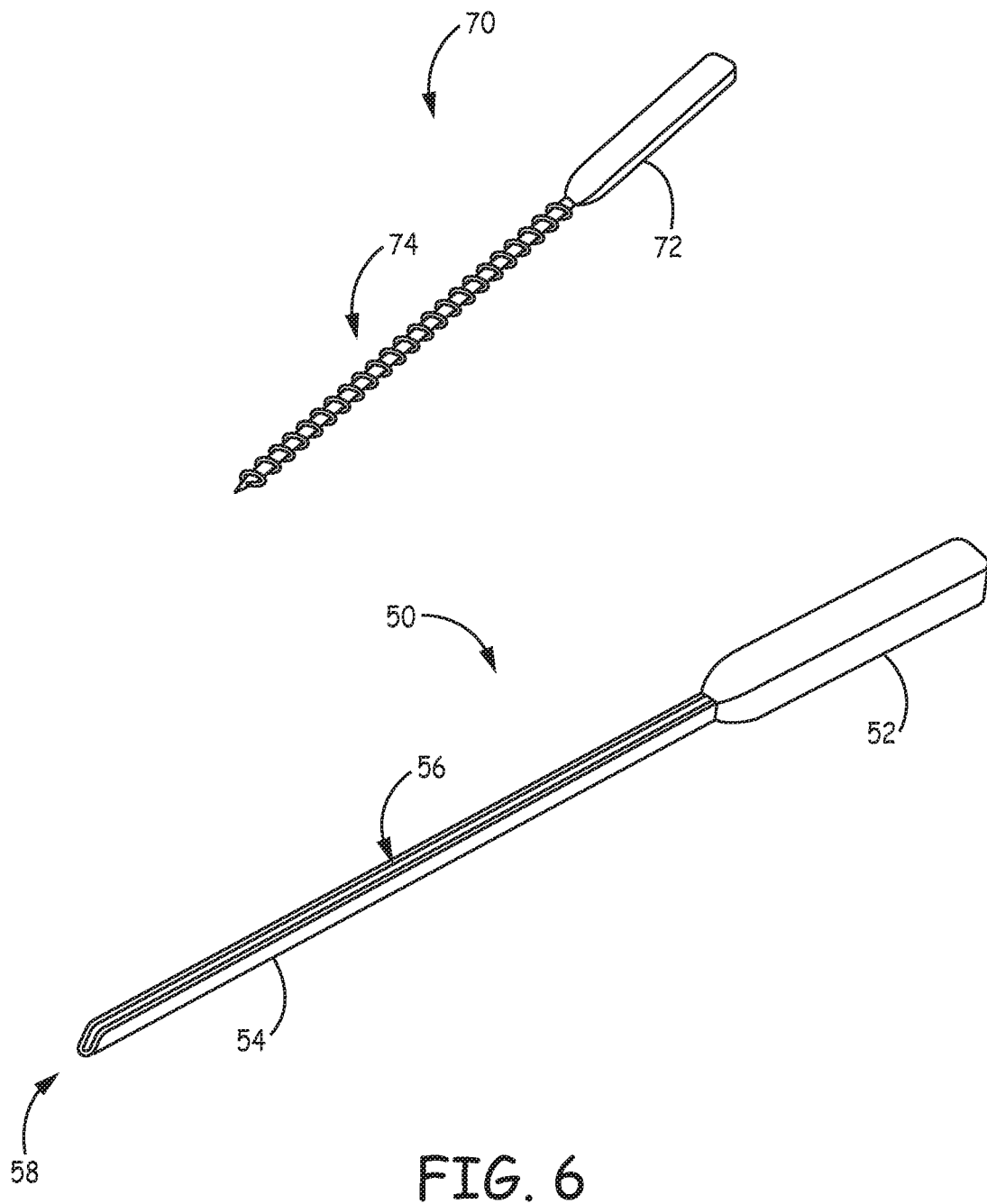
FIG. 6 is a schematic diagram illustrating another implant tool that includes an open channel delivery tool and another example bore-in mechanism.

FIG. 6 is a schematic diagram illustrating another implant tool that includes open channel delivery tool 50 and another example bore-in mechanism 70. Bore-in mechanism 70, which is also illustrated FIG. 7, includes a handle 72 and a screw 74. Screw 74 includes a shaft 76 and a helical thread 78. Shaft 76 has a length L4 that extends from handle 72 to a distal end. Length L4 may be between approximately 1.5-6.0 inches in one example. However, length L4 may be less than 1.5 inches or greater than 6.0 inches in other instances. In some instances, at least a portion of shaft 76 may include a helical groove to receive helical thread 78. In one example, shaft 76 may be made of a polymer. In another example, shaft 76 may be made of a malleable metal or metal alloy.

Figure 7:
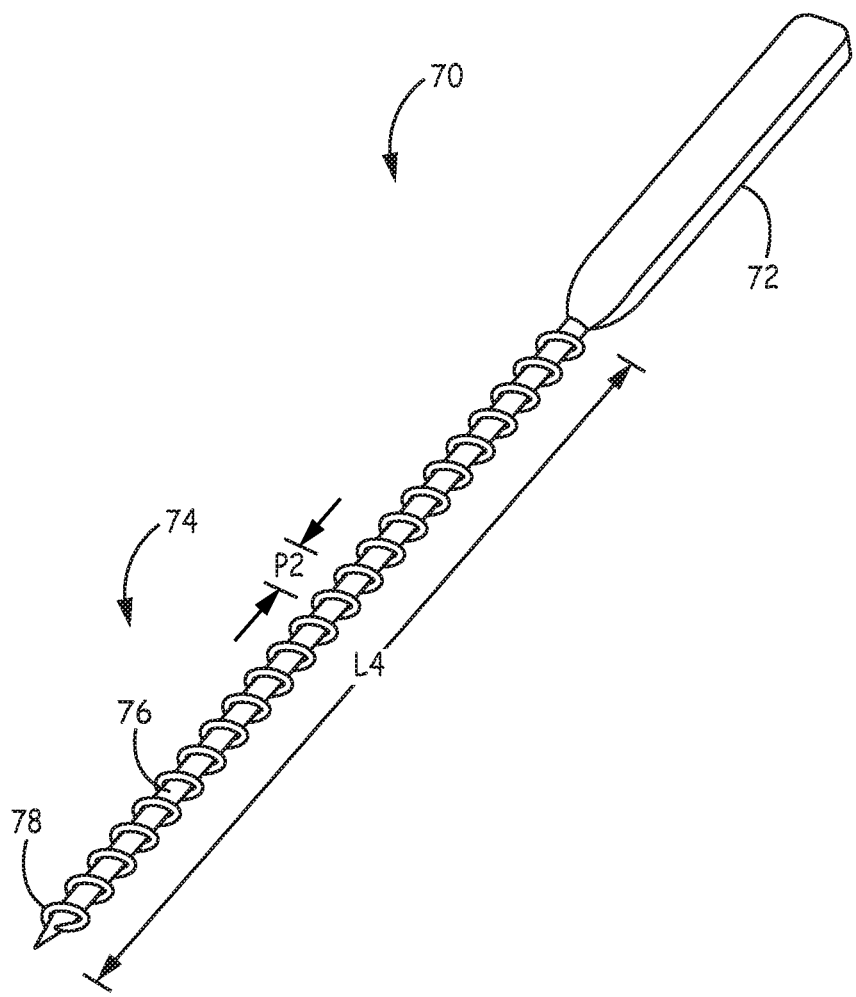
FIG. 7 illustrates an angled view of the bore-in mechanism of the implant tool of FIG. 6.

Helical thread 78 is illustrated in FIGS. 6 and 7 as extending along substantially the entire length L4 of shaft 76. In other instances, however, helical thread 78 may only extend along a distal portion of shaft 76. For example, helical thread 78 may only extend along approximately the distal one-third of shaft 76. Helical thread 78 has a pitch (P2), which is the width of one complete helix turn, and which may be between approximately 0.05-0.30 inches. Other pitches may be used in other embodiments however. Helical thread 78 may be made from a metal or metal alloy. In other instances, helical thread 78 may be made from a polymer.

Handle 72 may be constructed of metal, metal alloy, polymer, or other material or combination of materials. Handle 72 may be sized and shaped to fit within a hand and be ergonomically comfortable. Handle 72 may, for example, have a length between 1.5-6.0 inches. However, handle 72 may have lengths greater and less than this range without departing from the scope of this disclosure. Handle 72 of FIGS. 6 and 7 may have a number of sides, e.g., from 2-6 for example), may be a smooth cylindrical handle, a "T" handle, or other type of handle. The handle may also be formed to accommodate connection to open channel delivery tool 50.

Shaft 54 of open channel delivery tool 50 and bore-in mechanism 70 are sized such that screw 74 of bore-in mechanism 70 fits within open channel 56 of delivery tool 50. Thus, screw 74 may be constructed to have an outer diameter that is less than the inner diameter of open channel 56.

Open channel delivery tool 50 and bore-in mechanism 70 may be used in conjunction with one another to safely traverse the diaphragmatic attachments. In one example, open channel deliver tool 50 and bore-in mechanism 70 may be used together to access the substernal space. As will be described below, using the tools in conjunction with one another may allow traversing the diaphragmatic attachments while controlling momentum of the tool after the traversal of the attachments. In this manner, the implant tool allows traversing of the diaphragmatic attachments with a reduced likelihood of damage to surrounding organs.

Initially, an implanter or other user grips handle 72 and turns to screw the distal end of screw 74 into the diaphragmatic attachments near a center of the torso of patient 12 (e.g., just below the xiphoid process). In one example, the distal end of screw 74 does not traverse the diaphragmatic attachments. In another example, the distal end of screw 74 does traverse the diaphragmatic attachments.

After embedding screw 74 of bore-in mechanism 70 into the diaphragmatic attachments, open channel 56 of delivery tool 50 is placed adjacent to the portion of screw 74 exiting the patient body such that screw 74 resides within open channel 56. As described above, shaft 76 and helical thread 78 are capable of being flexed or bent. Bore-in mechanism 70 is pulled away from patient 12 while shaft 54 of open channel delivery tool 50 is advanced toward patient 12. By pulling bore-in mechanism 70 away from patient 12, the diaphragmatic attachments are pulled slightly away from chest cavity providing additional space for the distal end 58 of shaft 54 of delivery tool 50 to traverse after it passes through the diaphragmatic attachments. In this manner, the implant tool allows traversing of the diaphragmatic attachments with a reduced likelihood of damage to surrounding organs.

After traversing the diaphragmatic attachments with shaft 54 of open channel delivery tool 50, bore-in mechanism 70 is unscrewed from the diaphragmatic attachments and removed from open channel 56 and the body of patient 12. Distal end 58 of shaft 54 may be tunneled along the posterior side of the sternum to a desired location. Once at the desired location, the user may deliver an implantable electrical lead, such as defibrillation lead 16 of FIG. 1, catheter or other implantable structure in the tunnel or path formed by open channel delivery tool 50 by pushing the defibrillation lead 16 through open channel 56 of shaft 54 and then removing tool 50 while leaving defibrillation lead 16 in the path created by the implant tool.

Delivery tool 50 may be used to form a subcutaneous tunnel lateral between the center of the torso of the patient to a pocket on the left side of the patient. Lead 16 may be advanced along channel 56 and delivery tool 50 may be removed leaving the proximal portion of lead 16 in place along the lateral path. This may be done before or after the substernal tunneling. The connector of lead 16 may be connected to the ICD.

In other embodiments, bore-in mechanism 70 may be integrated within delivery tool 50. For example, bore-in mechanism 70 may be permanently mounted within open channel 56 of delivery tool 50 and capable of sliding along open channel 56. To achieve such a configuration, bore-in mechanism 70 may not have a handle or the handle may be the same handle as the delivery tool 50. In such a case, delivery tool 50 and/or bore-in mechanism 70 may include some sort of locking mechanism by which bore-in mechanism 70 may be fixed at the distal end during the boring and traversing process and then unlocked and slid to the proximal end of open channel 56 during the tunneling process. Moreover, delivery tool 50 may include some sort of trigger or other actuation mechanism for controllably moving bore-in mechanism 70 along open channel 56 and/or for moving shaft 54 relative to bore-in mechanism 70 to controllably traverse the diaphragmatic attachments. The trigger may, for example, move shaft 54 a fixed distance relative to bore-in mechanism 70 each time the trigger is actuated. The inner surface of shaft 54 forming open channel 56 may be threaded along at least a portion of the shaft 54 to match the threading of screw 74.

Various examples have been described. These and other examples are within the scope of the following claims.

The invention claimed is:

1. A system for implanting an implantable medical lead at least partially within a substernal space of a patient, the system comprising:
 a delivery tool separate from the implantable medical lead, the delivery tool comprising:
  a delivery tool handle; and
  a delivery tool shaft,
  wherein a proximal end of the delivery tool shaft is attached to the delivery tool handle,
  wherein the delivery tool shaft defines an open channel that is open along an entire section of the delivery tool shaft, the delivery tool shaft defining a width of the open channel, and the section extending from near the proximal end of the delivery tool shaft to a distal end of the delivery tool shaft, wherein the open channel terminates distal to a proximal end of the delivery tool handle, and wherein a cross-section of the delivery tool shaft at every point along the entire section is arc-shaped; and
 a bore-in mechanism separate from the implantable medical lead, the bore-in mechanism configured to interact with the delivery tool to access the substernal space, and the bore-in mechanism including a bore-in mechanism handle and a bore-in device extending from the bore-in mechanism handle,
 wherein the bore-in device includes a bore-in mechanism shaft supporting a helical component configured to advance into tissue of a patient as the bore-in mechanism rotates,
 wherein the delivery tool shaft is configured such that the width allows the bore-in mechanism shaft and the helical component to pass through the width to position within the open channel, and
 wherein the delivery tool shaft is configured such that the width prevents the bore-in mechanism handle from passing through the width to position within the open channel.

2. The system of claim 1,
 wherein a width of the open channel is greater than a maximum diameter of the implantable medical lead, and
 wherein a depth of the open channel is approximately equal to the maximum diameter of the implantable medical lead.

3. The system of claim 1, wherein the helical component comprises a helix.

4. The implant tool of claim 3, wherein a length of the helix is between approximately 1.5 and 3.5 inches.

5. The system of claim 1, wherein a distal end of the bore-in mechanism is sharp.

6. The system of claim 1, wherein the helical component comprises a helical thread extending along at least a portion of the bore-in mechanism shaft.

7. The system of claim 6, wherein the bore-in mechanism comprises a polymer, and wherein the helical thread comprises a metal or a metal alloy.

8. The system of claim 6, wherein the helical thread extends along a distal portion of the bore-in mechanism shaft.

9. The system of claim 1, further comprising the implantable medical lead, wherein the open channel is configured to establish a slight interference fit with the implantable medical lead when the open channel receives the implantable medical lead.

10. The system of claim 1, wherein the open channel terminates distal to a distal end of the delivery tool handle, wherein the distal end of the delivery tool handle is opposite the proximal end of the delivery tool handle.

11. The system of claim 1, wherein the bore-in mechanism shaft and the helical element are configured to bend when the width allows the bore-in mechanism shaft and the helical component to position within the open channel and the width prevents the bore-in mechanism handle from positioning within the open channel.

12. A system for implanting an implantable medical lead at least partially within a substernal space of a patient comprising:
 a delivery tool separate from the implantable medical lead, the delivery tool comprising:
  a delivery tool handle; and
  a delivery tool shaft,
  wherein a proximal end of the delivery tool shaft is adjacent to the delivery tool handle,
  wherein the delivery tool shaft defines an open channel that is an entire section of the delivery tool shaft, the delivery tool shaft defining a width of the open channel, and the section extending from near the proximal end of the delivery tool shaft to a distal end of the delivery tool shaft, the open channel terminating distal to a proximal end of the delivery tool handle, and
  wherein a cross-section of the delivery tool shaft at every point along the entire section is arc-shaped; and
 a bore-in mechanism separate from the implantable medical lead, the bore-in mechanism is configured to interact with the delivery tool to access the substernal space, and the bore-in mechanism including a bore-in mechanism handle and a bore-in device extending from the bore-in mechanism handle,
 wherein the bore-in device includes a bore-in mechanism shaft supporting a helical component configured to advance into tissue of the patient,
 wherein the delivery tool shaft is configured such that the width allows the bore-in mechanism shaft and the helical component to pass through the width to position within the open channel, wherein the delivery tool shaft is configured such that the width prevents the bore-in mechanism handle from passing through the width to position within the open channel, wherein the bore-in mechanism shaft and the helical element are configured to bend when the width allows the bore-in mechanism shaft and the helical component to position within the open channel and the width prevents the bore-in mechanism handle from positioning within the open channel, and wherein the helical component comprises a helical thread.

13. The system of claim 12, further comprising the implantable medical lead, wherein a width of the open channel is greater than a maximum diameter of the implantable medical lead.

14. The system of claim 12, wherein the helical component is configured to advance into the tissue as the bore-in mechanism rotates.

15. The system of claim 12, wherein the helical component comprises a helix.

16. The implant tool of claim 15, wherein a length of the helix extending from the bore in mechanism handle is between approximately 1.5 and 3.5 inches.

17. The system of claim 12 wherein a distal end of the helix of the bore-in mechanism is sharp.

18. The system of claim 12, wherein the helical component comprises a helical thread.

19. The system of claim 12, further comprising the implantable medical lead, wherein the open channel is configured to establish a slight interference fit with the implantable medical lead when the open channel receives the implantable medical lead.

* * * * *